United States Patent
Puts et al.

(10) Patent No.: US 7,970,187 B2
(45) Date of Patent: Jun. 28, 2011

(54) METHOD, APPARATUS AND COMPUTER PROGRAM FOR CONTOUR DETECTION OF VESSELS USING X-RAY DENSITOMETRY

(75) Inventors: Marcus Johannes Hubertus Puts, Landgraaf (NL); Jean-Paul Maria Michel Aben, Limbricht (NL); Boudewijn Joseph Angelus Verstraelen, Lanaken (BE)

(73) Assignee: Pie Medical Imaging B.V., Maastricht (NL)

( * ) Notice: Subject to any disclaimer, the term of this patent is extended or adjusted under 35 U.S.C. 154(b) by 1417 days.

(21) Appl. No.: 11/220,183

(22) Filed: Sep. 6, 2005

(65) Prior Publication Data

US 2007/0053558 A1 Mar. 8, 2007

(51) Int. Cl.
G06K 9/00 (2006.01)
G06K 9/36 (2006.01)
(52) U.S. Cl. ............ 382/128; 345/419; 348/42
(58) Field of Classification Search .......... 382/131, 382/128

See application file for complete search history.

(56) References Cited

U.S. PATENT DOCUMENTS

| | | | | |
|---|---|---|---|---|
| 6,047,080 A * | 4/2000 | Chen et al. | | 382/128 |
| 6,246,745 B1 * | 6/2001 | Bi et al. | | 378/54 |
| 6,438,201 B1 * | 8/2002 | Mazess et al. | | 378/56 |
| 6,532,380 B1 * | 3/2003 | Close et al. | | 600/431 |
| 6,621,917 B1 * | 9/2003 | Vilser | | 382/128 |
| 6,674,894 B1 * | 1/2004 | Parker et al. | | 382/154 |
| 7,099,520 B2 * | 8/2006 | Ishiguro | | 382/275 |
| 7,609,871 B2 * | 10/2009 | Ruth et al. | | 382/132 |
| 2004/0086175 A1 * | 5/2004 | Parker et al. | | 382/154 |
| 2005/0002546 A1 * | 1/2005 | Florent et al. | | 382/128 |
| 2007/0116342 A1 * | 5/2007 | Zarkh et al. | | 382/130 |

OTHER PUBLICATIONS

Quantification of Coronary Artery Lumen Volume by Digital Angiography, Sabee Molloi et al, Circulation Nov. 6, 2001, pp. 2351-2357.
CAAS II : A Second Generation System for Off-Line and On-Line Quantitative Coronary Angiography; Ed Gronenschile, et al, Cauterization and Cardiovascular Diagnosis 33:61-75 (1994).
Are Two Distributions Different?, *Numerical Recipes in C: The Art of Scientific Computing* ©, Chapter 14.3, pp. 620-628, 1992.

* cited by examiner

*Primary Examiner* — Hadi Akhavannik
(74) *Attorney, Agent, or Firm* — Gordon & Jacobson, PC (57) ABSTRACT

A method has been described for deriving contour data in X-Ray images for vessels with differential absorption through applying a contour-finding algorithm on a shadow image and finding the vessel borders through segmentation based on image intensities. In particular, the method uses the following steps: finding a densitometric area of an above mentioned vessel, and displacing one or both of the borders inward until the densitometric measurement result between the borders after such displacing will start to change significantly. Furthermore, a specific procedure is introduced to automatically determine the conversion factor to equate the densitometrically based diameter to the contour based diameter of the vessel and to discriminate bifurcating or parallel vessels.

39 Claims, 5 Drawing Sheets

METHOD, APPARATUS AND COMPUTER PROGRAM FOR CONTOUR DETECTION OF VESSELS USING X-RAY DENSITOMETRY

BACKGROUND OF THE INVENTION

The invention relates generally to computer-based methods for deriving contour data for vessels with differential absorption utilizing x-ray densitometry, and more particularly to such computer-based methodologies that detect vessel contours by the application of a contour-finding algorithm on a shadow image and segmentation based on image intensities. A prime field of application for such computer-based methodologies is in small, in particular sub-millimeter blood vessels. However, such computer-based methodologies may also be used for other vessels that may have differential X-Ray attenuation or for implanted objects such as stents. Such finding of contours or borders is standard technology in medical diagnostics and related arts.

Prior art, in particular, S. Molloi et al, Quantification of Coronary Artery Lumen Volume by Digital Angiography, © 2001 to the American Heart Association, Reprints from symolloi@uci.edu, have described that contour detection methods based on local grayscale levels can result in different diameter estimations than methods that measure the total attenuation of radiation caused by the vessel for use as an estimation of the cross sectional area. For a normal round vessel the latter will then also produce an estimate for the diameter. The reference makes however no systematic use of this finding.

The present inventors have experienced that sometimes vessels are identified as being too large when contour detection is based on local intensities (for instance a minimum cost algorithm is used, as mentioned in Gronenschild, E, et al., 1994, A Second Generation System for Off-Line and On-Line Quantitative Coronary Angiography. Catheterization and Cardiovascular Diagnosis 33:61-75). Generally, these over-estimations are caused by noise and blur in the X-ray image. Especially in smaller vessels with diameters less than about 1 mm the effect is noticeable.

Such apparent enlargement of a vessel may compromise the diagnostics of inter alia coronary stenosis or may influence the results of studies on the efficiency of new clinical treatments. Note that other vessel locations than coronary arteries will be influenced in the same way and can benefit correspondingly from improvements.

SUMMARY TO THE INVENTION

The inventors have furthermore recognized that the overall amount of radiation that is absorbed by the object stays constant under varying conditions of noise and blur. By itself, noise and blur are well-known phenomena that can be caused by sampling or various external phenomena. Although the image is blurred, the sum of the intensities over the vessel stays the same. Hence, the determination of the vessel border position as based on the above contour-finding algorithm could be improved by shifting these borders until the sum of the intensities between the borders corrected for the background image value starts to change significantly. According to this basic method, the cross-sectional shape of the vessel is irrelevant. Therefore, according to one of its objectives, the invention proposes a method to merge the densitometric information with the contour based information to generate much more accurate borders for the vessel.

Now therefore, according to one of its aspects, the invention is characterized by finding a densitometric area of a blood vessel and selectively displacing one or both of the borders of the vessel inward until the densitometric measurement result between the borders after such displacing will start to change significantly.

According to a further aspect, under the assumption that the vessel has a known cross-sectional geometric shape (e.g., a circular shape), the densitometric information can be used to estimate the width of the vessel in question directly. This measure will simplify the processing and is in general accurate.

Advantageously, the invention for a predetermined vessel segment automatically finds a conversion factor between a densitometrically derived vessel diameter and a vessel diameter based on contour detection. Such conversion factor is found by fitting a first cumulative histogram of diameters found by contour detection with a second cumulative histogram of diameters found by the densitometry. This statistical processing is a mature art and will lead to a robust result of the operation.

A related problem considers the occurrence of parallel, bifurcated, or crossing vessels. In such situation, sometimes a contour detection algorithm may trace the outer boundaries of both vessels as being combined, leading to a much too wide vessel. In fact, the above-mentioned over-estimating of the vessel size will occur, sometimes by quite a large factor. Therefore, an additional measure is taken by the invention to solve this specific point. More particularly, the computer-based methodology of the present invention can be extended to discriminate mutually distinct blood vessels located between found borders that show an intermediate densitometric dip.

The invention also relates to an apparatus and computer program for carrying out operations that detect the contour of a blood vessel as described herein.

BRIEF DESCRIPTION OF THE DRAWING

These and further features, aspects and advantages of the invention will be discussed more in detail hereinafter with reference to the disclosure of preferred embodiments of the invention, and in particular with reference to the appended figures that illustrate.

DETAILED DESCRIPTION OF PREFERRED EMBODIMENTS

Hereinafter, a preferred embodiment of the invention will be discussed in detail. The reason why the contour detection goes wrong is that the contours may in certain areas have too little contrast. Although many other routes can be followed to determine if enough contrast is present, the inventors have by way of example used a Student's t-test for independent groups. An advantage of such statistical test is that it will also take the numbers of pixels into account. The Student's t-test is a statistical test that determines if the pixel values inside the found vessel differ statistically significantly from pixel values outside the vessel. A scan line is defined through the vessel that is approximately perpendicular to the local centerline of the vessel. Along this scan line the average pixel values inside the found vessel ($\mu_{in}$) and outside the found vessel ($\mu_{out}$) as well as the standard deviations inside ($\sigma_{in}$) and outside the found vessel ($\sigma_{out}$) are determined on the basis of $n_{in}$ pixels inside and $n_{out}$ pixels outside the vessel. Various procedures may be used to determine a centerline of the vessel, and the actual position of the scan line. Based on the above, the t-value is calculated:

$$t_{in,out} = \frac{\mu_{in} - \mu_{out}}{\sqrt{\left(\frac{(n_{in}-1)\sigma_{in}^2 + (n_{out}-1)\sigma_{out}^2}{n_{in}+n_{out}-2}\right)\left(\frac{1}{n_{in}}+\frac{1}{n_{out}}\right)}} \tag{1}$$

When the p-value associated with this t-value is larger than a certain threshold, pixels inside the vessel found do not differ statistically significantly from the pixels outside the vessel. Note that every analysis that quantifies the Signal-to-Noise ratio can be used to signify the strength of the contours. An advantage of the Student's t-test is that it corrects for the numbers of samples (in this case numbers of pixels).

A problem with densitometry is that, when two vessels cross or lie otherwise in each other's neighborhood, the densitometry can estimate the real diameter as being too large. For that reason, a further criterion is added: when the densitometry gives a larger diameter than the contour detection, contour detection is used without taking recourse to densitometry.

Summarizing, we can say that the densitometry is used if and only if the pixel values outside the vessel differ statistically significantly from the pixel values inside the vessel and moreover, the contour based diameter is larger than the diameter based on densitometry:

$$\text{UseDens}(\bar{x}) \Leftrightarrow [t_{in,out}(\bar{x}) > \alpha] \hat{} [D_{contour}(\bar{x}) > D_{dens}(\bar{x})] \tag{2}$$

The position of the borders is corrected in two steps. First, the absolute width of the vessel is adjusted according to the densitometry. Subsequently, the position of the border(s) is shifted until it matches the vessel better.

Scaling the borders around the centerline so that the width is equal to the densitometric diameter changes the width of the vessel is then effected according to:

$$\text{UseDens}(\bar{x}) \Rightarrow \begin{cases} \bar{x}_{center} + \frac{D_{dens}}{D_{contour}}(\bar{x}_{left} - \bar{x}_{center}) \rightarrow \bar{x}_{left} \\ \bar{x}_{center} + \frac{D_{dens}}{D_{contour}}(\bar{x}_{right} - \bar{x}_{center}) \rightarrow \bar{x}_{right} \end{cases} \tag{3}$$

Finally, the new borders will be moved along the scan line until the found average within the borders is minimal:

$$\begin{cases} \bar{x}_{left} + \zeta(\bar{x}_{left} - \bar{x}_{right}) \rightarrow \bar{x}_{left} \\ \bar{x}_{right} + \zeta(\bar{x}_{left} - \bar{x}_{right}) \rightarrow \bar{x}_{right} \end{cases} \tag{4}$$

where $\zeta$ is the parameter which describes the shift along the scan line.

Herein, $\zeta$ is determined by minimizing the sum of pixel intensities between the left and right hand borders:

$$\min_{\zeta} \arg \int_0^1 I(\bar{x}_{left} + (\zeta + z)(\bar{x}_{left} - \bar{x}_{right}))dz \tag{5}$$

Note that for a certain choice of $\zeta$, only one border will move. When two vessels are close to each other and are more or less parallel, the minimum cost algorithm sometimes sees the two vessels as a single one. Even though the densitometry gives a much smaller diameter, the latter may still be overestimated. This "parallel vessel problem" has by an extension of the invention been solved as well.

Detecting of parallel vessels is sometimes difficult. However, detecting a gap between vessels is relatively easy. When scanning pixels along a scan line running across a single vessel, the maximum density should be in the middle of the vessel instead of at a boundary of the vessel. A parallel vessel or combined vessel is present when such maximum density is not in the middle. One possibility is the occurrence of a substantial density dip somewhere between the borders, such as by an amount of at least 5%, 10% or another value suited to the situation in case. This can lead to concluding of two clearly separated vessels, such as parallel vessels or a bifurcation. Another possibility is a very asymmetric density profile. This could be caused by two vessels of which one lies in part behind the other. Such situation could be signaled to the user as an exceptional one. Note that if the vessel in question is filled with a lower-density fluid than the surrounding tissue such as $CO_2$ gas instead of iodine contrast fluid, the density values used for processing should be inverted.

Correcting a vessel is done in two stages. In the first stage, the borders between the left and the right boundary are allocated. These borders can be represented by a transition from a low density to a high density (in the set $C_{lh}$) and conversely, from high density to low density (in the set $C_{hl}$):

$$\begin{cases} \bar{x} \in C_{lh} \Rightarrow \bar{c}_r = \frac{1}{2}(\bar{x} + \bar{x}_{left}) \\ \bar{x} \in C_{hi} \Rightarrow \bar{c}_l = \frac{1}{2}(\bar{x} + \bar{x}_{right}) \end{cases} \tag{6}$$

The right border is selected by determining the new centerline point and comparing it with the original centerline point:

$$\begin{cases} \min_{x \in C_{ih}} \arg d\left(\frac{1}{2}(\bar{x} + \bar{x}_{left}), \ell_{center}\right) \\ \min_{x \in C_{hi}} \arg d\left(\frac{1}{2}(\bar{x} + \bar{x}_{right}), \ell_{center}\right) \end{cases} \tag{7}$$

If the found distance is beneath a certain threshold, we select this point as a potential new border point. The point in between the original boundary point and the newly calculated point is used as a point on a restriction line.

To use the densitometric data for estimating the cross-sectional area of a vessel, we need to find the conversion factor between the densitometric units and the contour based area in mm$^2$, under the assumption that the vessel is circular. Suppose that a vessel has a contour based circular area (in mm$^2$) $A_{circ}$, and a densitometric area (in densitometric units) $A_{dens}$. The resulting conversion factor is then equal to $A_{circ}/A_{dens}$.

In general, the conversion factor can be found by fitting the circular area to the densitometric area that is scaled by the conversion factor:

$$\operatorname*{minarg}_{c} Q(S(\overline{A}_{circ}), S(x\overline{A}_{dens})) \quad (8)$$

Here c is the conversion factor, S is a statistic on the areas, and Q is a function to quantify the difference between the two found area profiles. Q can be the sum of squared difference between the two areas. However, taking one representative as a statistic can lead to the incorrect choice, which makes the result less robust. For that reason, it was chosen to take a statistic that represents all the data. In a histogram, the number of occurrences as a function of the area is described in a list of tuples $<A,n>_m$. Because a histogram can be multimodal, we use a cumulative histogram:

$$s = \left\{ A_m N_m | A_m \in R \wedge N_m = \sum_{i=1}^{m} n_m \right\}^M \quad (9)$$

The bins defined in this histogram have a size of $A_m$-$A_{m-1}$. For Q we have several options. Some well-known measures for cumulative histograms are Kolmogorov-Smirnov D and Kuiper D (see e.g., W.H. Press et al, Numerical Recipes: The art of scientific computing, Cambridge University Press 1992, pp. 620-628). However, these procedures only look at the extremes of the differences. Therefore, it is preferred to analyze the complete cumulative histograms. Therefore we choose:

$$Q(\Delta S, w) = \Sigma_A w_A |\Delta N_A| \quad (10)$$

Herein, w is a weighting function. Since generally, the smallest and largest diameters in the set are less reliable, the weighting function should give a lower weight to the smallest diameters and largest diameters. This is done by choosing $w_A = ((1+\omega)N_{max} - N_{A,circ})N_{A,circ}$. Herein, $\omega$ is a weight factor for the largest diameters, which factor is set to 0.1.

Combining equation (8), (9) and (10) gives:

$$\operatorname*{minarg}_{c} \sum_A ((1+\omega)N_{max} - N_{\overline{A}_{circ}}(A)) N_{\overline{A}_{circ}}(A) |N_{\overline{A}_{circ}}(A) - N_{c\overline{A}_{dens}}(A)| \quad (11)$$

The cumulative histogram for the densitometric area scales with c, which means that the histogram needs to be recalculated for each value of c. Therefore, the process can be made faster by sampling the areas on a log scale.

This means that the densitometric area histogram needs to be calculated only once and the time-consuming scaling is changed into a shift of the log densitometric area histogram.

Now, the correcting is effected in three steps. In the first two it is decided when the contour has to be corrected. Finally, the algorithm decides where the borders must be positioned. The first part is effectively detecting that the contour detection goes wrong, whereas the latter part is about what went wrong during contour detection.

Figure 1:
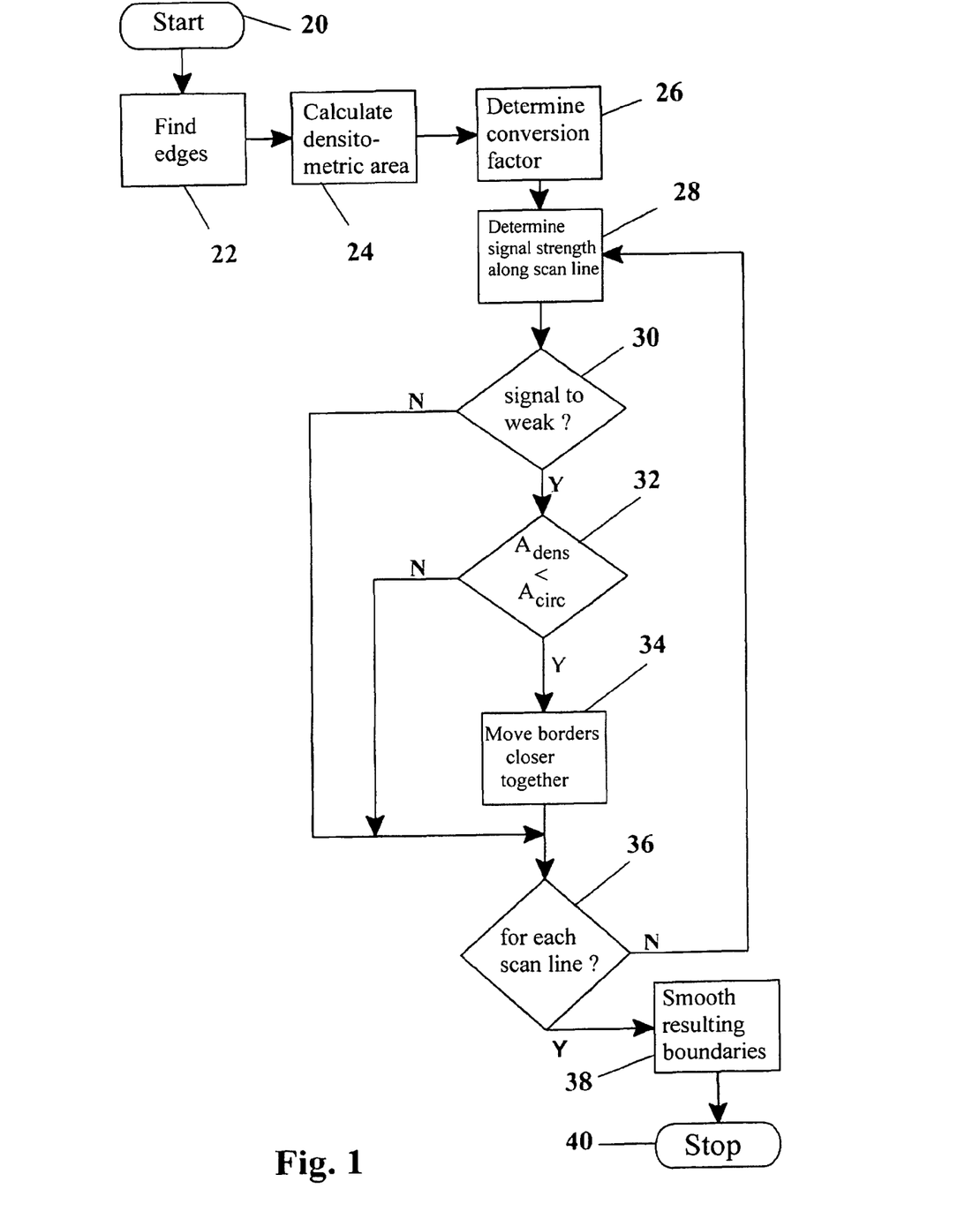
FIG. 1, a flow diagram of applying the inventive method.

FIG. 1 illustrates an example of a flow diagram of applying the inventive method. Note that the radiologic apparatus and the associated computer facilities can be standard and will in consequence herein not be discussed in detail. Such apparatus would by itself be obvious to the skilled art practitioner. In the preferred embodiment, the inventive methodology described herein is stored as a software application on program storage device (e.g., CD-ROM disc, DVD disc, magnetic tape, magnetic disk drive, etc). The software application, which is realized by a programmed sequence of instructions, is loaded onto a hard disk drive (or other program storage device) of a computer system for execution by the computer processing platform (CPU/memory system) of the computer system as is well known. In block 20, the data processing starts and the necessary hardware and software facilities are claimed. In block 22, the border is detected. Before the contour detection starts, the user indicates a segment and, for this segment, a centerline is determined. On the basis of this centerline, the vessel borders are detected through standard segmentation methods.

Furthermore, in block 24, the densitometric area is calculated in a direction along the centerline. For each position along the centerline, the amount of radiation absorbed by the vessel, relative to the background is determined. The logarithm of this absorption coefficient is proportional to the cross sectional area of the vessel, which is called the densitometric area.

Figure 2A:
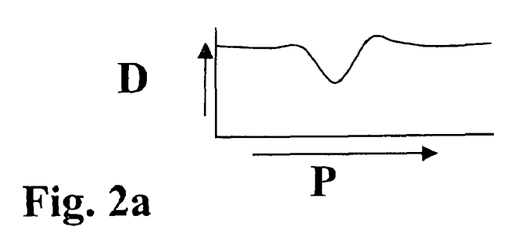
FIGS. 2a-2d, the determining of a conversion factor between contour based and densitometric results.
Figure 2B:
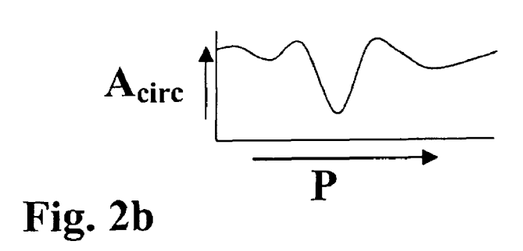
Figure 2C:
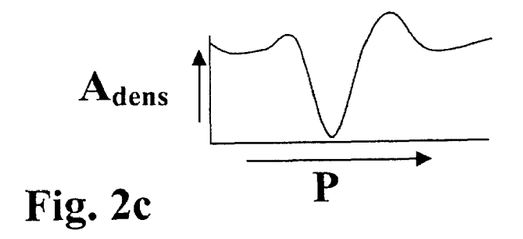
Figure 2D:
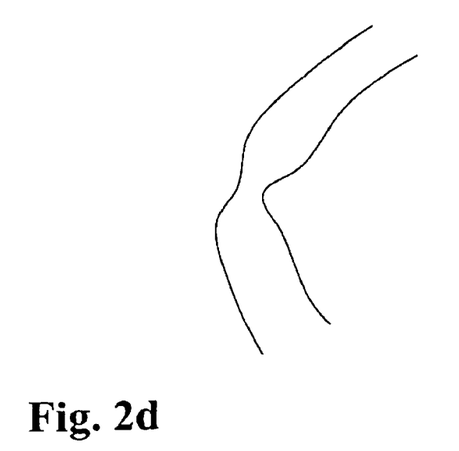

Next, in block 26, a conversion factor between the densitometric area and the area between the borders is calculated. The latter is postulated as being circular ('circular area'). In this respect, FIGS. 2a-2d illustrate the determining of a conversion factor between contour based and densitometric results. The figures are qualitative only. FIG. 2d forms a "real" illustration of a vessel, showing that the diameter is apparently non-uniform along the vessel. FIG. 2a illustrates the diameter D along the centerline position P of the vessel shown in FIG. 2d. FIG. 2b also as a function of the position P along the centerline illustrates the circular area $A_{circ}$. FIG. 2c again as a function of the position P along the centerline illustrates the densitometric area $A_{dens}$ as based on the densitometric data. Scaling FIG. 2c to FIG. 2b, will yield a single conversion factor along the whole length of the vessel section.

Now, block 28 is executed on each scan line. For each scan line, the strength of the vessel is determined. This strength is governed by comparing the distribution of pixel intensities inside the vessel to the pixel intensities outside the vessel. The strength is proportional to the differences between these pixel intensity distributions.

Now, the above operations can be done by means of the statistical method as described in eq. (1), or by any other suitable method. If they do differ statistically significantly (as determined in block 30), the next scan line across the vessel centerline is selected when there is still a scan line available (block 36). Otherwise it is checked whether the densitometric area is smaller than the circular area (block 32).

If so, one or two of the borders are moved closer together (block 34) as described in eqs. 3, 4 and 5. Alternatively, different procedures for moving the borders could be used. After producing all of the borders, in block 38 the resulting borders are smoothed. By themselves methods therefore are standard technology. Finally, in block 40, the process is terminated.

Figure 3:
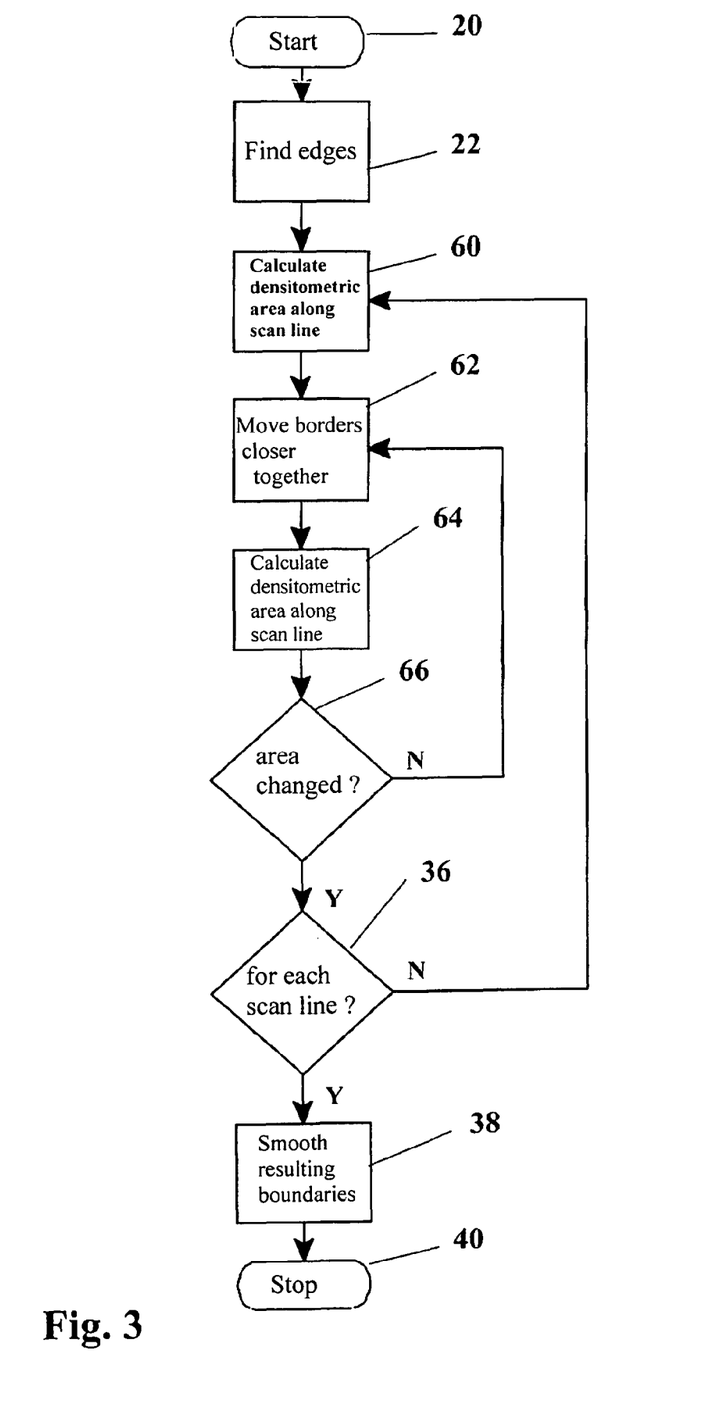
FIG. 3, a further flow diagram of applying the inventive method.

FIG. 3 illustrates another approach. In particular, the procedure can be iterative on a geometrical level.

First, blocks 20, 22 correspond to FIG. 1 and will not be discussed further. In block 60, for as many points of the centerline as deemed necessary, a scan line is set up that is substantially perpendicular the local centerline orientation. Now, the densitometric area is calculated along the scan line, which is obviously a function of position along the centerline.

Next, in block 62, the segmentation borders are moved closer together. In block 64, the remaining densitometric area between the (moved) borders is calculated. In block 66, the system detects whether the densitometric area has changed. If not, the system loops back to block 62. The criterion for detecting of change in block 66 can be set at any appropriate level.

If the processing of the scan line has been finished, the system goes to block 60. Generally, the procedures of blocks 36, 38, 40 correspond to FIG. 1 and are not discussed here.

Figure 4A:
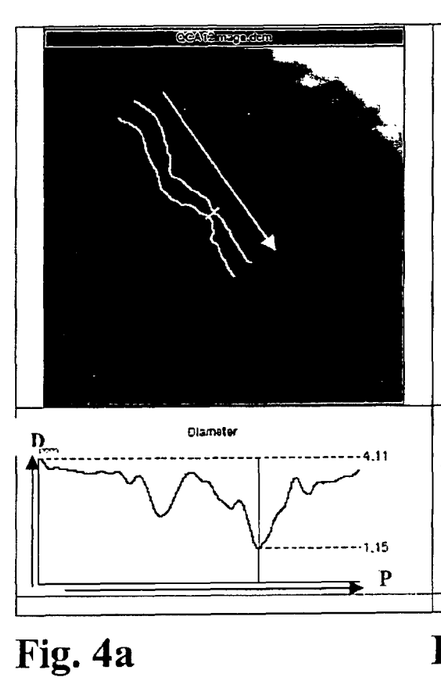
FIG. 4a, an X-Ray image produced through using only the prior art contour calculation.

FIG. 4a illustrates a coronary X-Ray image processed by using only the prior art contour calculation with contrast fluid having been applied to the vessel(s). The light non-straight lines indicate the borders of the vessel found by a segmentation process. The minimum diameter between the borders is indicated by a perpendicular light line in the figure. Below the image, a graph of the actually found diameter is shown. Plotted is the diameter D as a function of the position P, the latter in a direction in accordance with the light arrow along the vessel in the image above the graph.

Figure 4B:
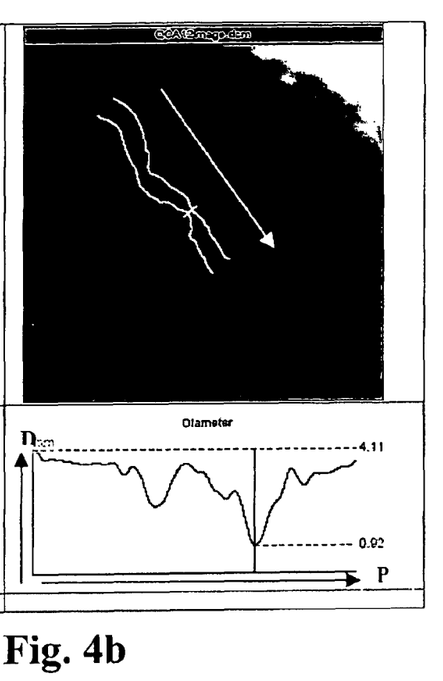
FIG. 4b, the same produced therefrom through using the invention.

FIG. 4b illustrates the result produced from the same specimen image but through using the improvement according to the invention. Generally, the diameters are corresponding, but especially in narrow passages, the invention results in values that are some 20% less or even lower. In certain clinical situations, such may represent a great difference. In the Figures, the overall diameter has been indicated in arbitrary units.

Figure 5A:
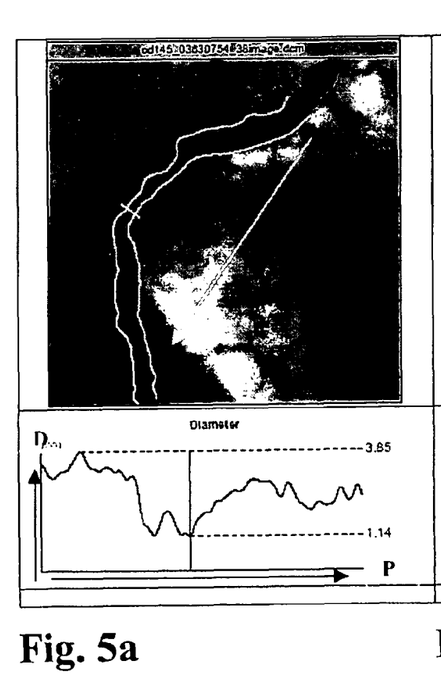
FIGS. 5a, 5b corresponding results attained for another image.
Figure 5B:
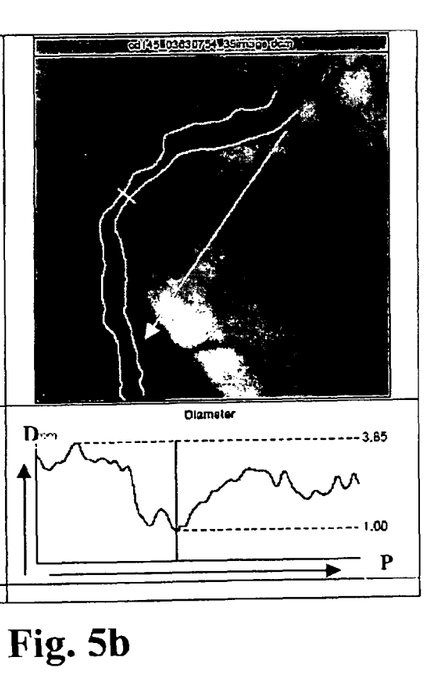

FIGS. 5a, 5b illustrate corresponding results attained for another image, represented in the manner discussed before for FIG. 4. Note in particular that the position of minimum diameter can shift somewhat along the vessel in question, through using the invention.

Figure 6A:
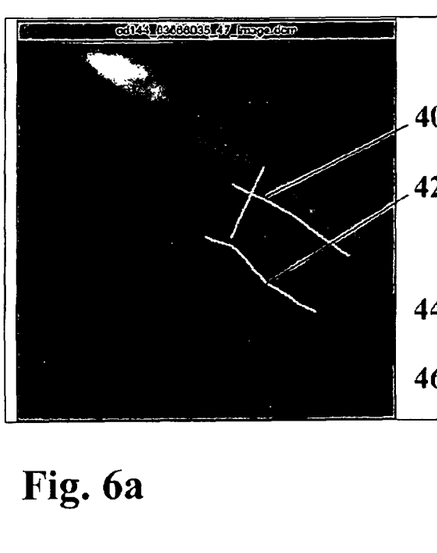
FIGS. 6a, 6b, the same results attained for a set of parallel vessels.
Figure 6B:
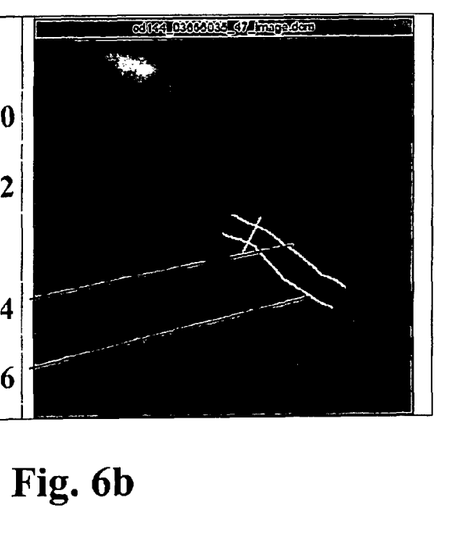

FIGS. 6a, 6b illustrate the same results attained for a parallel set of vessels. In FIG. 6a borders 40 and 42 show the overestimation of the vessel by the parallel vessel problem resulting in a seemingly "thick" vessel. FIG. 6b illustrates the result produced from the same image but through using the improvement according to the present invention. Through detecting an intermediate density dip, a single, much narrower vessel can be distinguished with edges 44, 46.

Figure 7A:
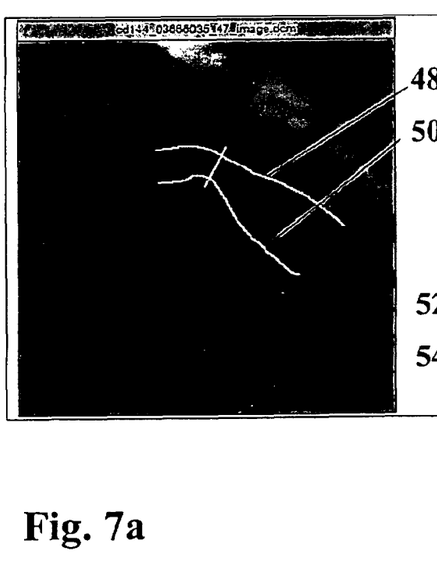
FIGS. 7a, 7b, the same results attained for a set of bifurcating vessels.
Figure 7B:
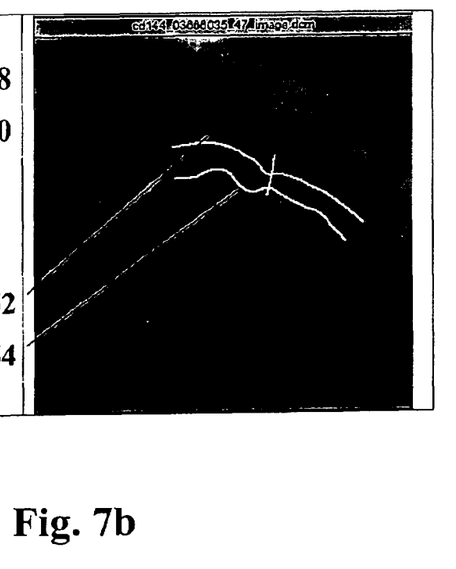

FIGS. 7a, 7b illustrate the detection of bifurcating vessels. Again in FIG. 7a, an overestimation of the vessel is visible with edges 48, 50. FIG. 7b illustrates the result (52,54) produced from the same image but through using the improvement according to the present invention. Through finding an intermediate density dip along part of the scan line, that sub-section is shown as consisting of two separated vessels, whereas the remainder retains it original shape. The addressing of two different situations in what is effectively more or less the same image has resulted from the different selections of the centerline.

Now, the present invention has here above been disclosed with reference to preferred embodiments thereof. Persons skilled in the art will recognize that numerous modifications and changes may be made thereto without exceeding the scope of the appended Claims. In consequence, the embodiments should be considered as being illustrative, and no restriction should be construed from those embodiments, other than as have been recited in the Claims.

The invention claimed is:

1. A method for deriving data characterizing the contour of a vessel portion in at least one x-ray image, the method performed by a data processing system with access to image data representing the at least one x-ray image, the method comprising:
   a) processing the image data to detect by segmentation borders of the vessel portion and a centerline of the vessel portion;
   b) processing the image data to derive densitometric areas for centerline positions along the length of the vessel portion; and
   c) displacing positions of at least one border of the vessel portion as derived in a) relative to corresponding centerline positions as derived in a) based upon the densitometric areas of the corresponding centerline positions as derived in b).

2. A method according to claim 1, further comprising:
   d) displaying a visual representation of the borders of the vessel portion on the x-ray image, the visual representation accounting for the position of the at least one border displaced in c).

3. A method according to claim 1, wherein:
the densitometric areas are derived from the amount of radiation absorbed by the vessel portion relative to a background.

4. A method according to claim 3, wherein:
at a given centerline position of the vessel portion, the logarithm of the amount of radiation absorbed by the vessel portion at the given centerline position relative to the background is proportional to the densitometric area at the given centerline position.

5. A method according to claim 1, wherein:
said densitometric areas assume a circular shape of the vessel portion.

6. A method according to claim 1, further comprising:
subsequent to the displacing of c), subjecting the borders of the vessel portion to a smoothing operation.

7. A method according to claim 1, wherein:
the displacing of c) is performed for a border position corresponding to a given centerline position only if a contour-based area is larger than the densitometric area for the given centerline position.

8. A method according to claim 1, wherein:
the method is used to discriminate mutually distinct blood vessels located between found borders that show an intermediate densitometric dip.

9. A method according to claim 1, wherein:
the method is used in quantitative arterial analysis.

10. A method according to claim 1, wherein:
the vessel portion comprises a sub-millimeter blood vessel.

11. A method according to claim 1, wherein:
the vessel portion comprises an implanted object that has a distinct X-ray absorption characteristic.

12. A method according to claim 1, wherein:
the border position corresponding to a given centerline position that is displaced in c) is defined by intersection of a scan line on the border, wherein the scan line is orthogonal to the centerline at the given centerline position.

13. A method according to claim 1, wherein:
the displacing of c) involves deriving a conversion factor between a densitometric area and a contour area based on said segmentation.

14. A method according to claim 13, wherein:
said conversion factor is found by fitting a first cumulative histogram of contour areas found by segmentation with a second cumulative histogram of densitometric areas.

15. A method according to claim 14, wherein:
said conversion factor is derived by fitting a statistic quantity between densitometric areas and contour areas through calculating $$\min \arg_c Q(S(A_{circ}) - S(cA_{dens})),$$

wherein $A_{dens}$ is a densitometric area, $A_{circ}$ is a contour area found by segmentation, c is the conversion factor, S is a statistic on the areas, and Q is a difference function that quantifies the difference between the densitometric area $A_{dens}$ and the contour area $A_{circ}$.

16. A method according to claim 1, wherein:
the displacing of c) involves
   i) displacement of at least one border inward relative to a given centerline position of the vessel portion, and
   ii) recalculating the densitometric area for the given centerline position of the vessel portion according to the inward displacement of the at least one border in i).

17. A method according to claim 16, wherein:
the operations of i) and ii) are repeated for zero or more iterations until there is predetermined change in the densitometric area.

18. An apparatus for deriving data characterizing the contour of a vessel portion in at least one x-ray image represented by image data, the apparatus comprising:
   a) means for processing the image data to detect by segmentation borders of the vessel portion and a centerline of the vessel portion;
   b) means for processing the image data to derive densitometric areas for centerline positions along the length of the vessel portion; and
   c) means for displacing positions of at least one border of the vessel portion as derived by the means of a) relative to corresponding centerline positions as derived by the means of a) based upon the densitometric areas of the corresponding centerline positions as derived by the means of b).

19. An apparatus according to claim 18, further comprising:
   d) means for displaying a visual representation of the borders of the vessel portion on the x-ray image, the visual representation accounting for the position of the at least one border displaced by the means of c).

20. An apparatus according to claim 18, wherein:
the densitometric areas are derived from the amount of radiation absorbed by the vessel portion relative to a background.

21. An apparatus according to claim 18, wherein:
at a given centerline position of the vessel portion, the logarithm of the amount of radiation absorbed by the vessel portion at the given centerline position relative to the background is proportional to the densitometric area at the given centerline position.

22. An apparatus according to claim 18, wherein:
the means c) displaces a border position corresponding to a given centerline position only if a contour-based area is larger than the densitometric area for the given centerline position.

23. An apparatus according to claim 18, wherein:
the border position corresponding to a given centerline position that is displaced by the means of c) is defined by intersection of a scan line on the border, wherein the scan line is orthogonal to the centerline at the given centerline position.

24. An apparatus according to claim 18, wherein:
the displacing of c) involves deriving a conversion factor between a densitometric area and a contour area based on said segmentation.

25. An apparatus according to claim 24, wherein:
said conversion factor is found by fitting a first cumulative histogram of contour areas found by segmentation with a second cumulative histogram of densitometric areas.

26. An apparatus according to claim 25, wherein:
said conversion factor is derived by fitting a statistic quantity between densitometric areas and contour areas through calculating $$\min \arg_c Q(S(A_{circ}) - S(cA_{dens})),$$

wherein $A_{dens}$ is a densitometric area, $A_{circ}$ is a contour area found by segmentation, c is the conversion factor, S is a statistic on the areas, and Q is a difference function that quantifies the difference between the densitometric area $A_{dens}$ and the contour area $A_{circ}$.

27. An apparatus according to claim 18, wherein:
the displacing means c) involves
   i) displacement of at least one border inward relative to a given centerline position of the vessel portion, and
   ii) recalculating the densitometric area for the given centerline position of the vessel portion according to the inward displacement of the at least one border in i).

28. An apparatus according to claim 27, wherein:
the operations of i) and ii) are repeated for zero or more iterations until there is predetermined change in the densitometric area.

29. A computer program medium that is installable onto a computer processing platform, the computer program medium readable by the computer processing platform, tangibly embodying a non-transitory program of instructions executable by the computer processing platform to perform methods steps for deriving data characterizing the contour of a vessel portion in at least one x-ray image represented by image data, the method steps comprising:
   a) processing the image data to detect by segmentation borders of the vessel portion and a centerline of the vessel portion;
   b) processing the image data to derive densitometric areas for centerline positions along the length of the vessel portion; and
   c) displacing positions of at least one border of the vessel portion as derived in a) relative to corresponding centerline positions as derived in a) based upon the densitometric areas of the corresponding centerline positions as derived by b).

30. A computer program medium according to claim 29, wherein the method steps further comprise:
   d) displaying a visual representation of the borders of the vessel portion on the x-ray image, the visual representation accounting for the position of the at least one border displaced in c).

31. A computer program medium according to claim 29, wherein:
the densitometric areas are derived from the amount of radiation absorbed by the vessel portion relative to a background.

32. A computer program medium according to claim 29, wherein:
at a given centerline position of the vessel portion, the logarithm of the amount of radiation absorbed by the vessel portion at the given centerline position relative to the background is proportional to the densitometric area at the given centerline position.

33. A computer program medium according to claim 29, wherein:
the displacing of c) is performed for a border position corresponding to a given centerline position only if a contour-based area is larger than the densitometric area for the given centerline position.

34. A computer program medium according to claim 29, wherein:

the border position corresponding to a given centerline position that is displaced in c) is defined by intersection of a scan line on the border, wherein the scan line is orthogonal to the centerline at the given centerline position.

35. A computer program medium according to claim 29, wherein:

the displacing of c) involves deriving a conversion factor between a densitometric area and a contour area based on said segmentation.

36. A computer program medium according to claim 35, wherein:

said conversion factor is found by fitting a first cumulative histogram of contour areas found by segmentation with a second cumulative histogram of densitometric areas.

37. A computer program product according to claim 36, wherein:

said conversion factor is derived by fitting a statistic quantity between densitometric areas and contour areas through calculating $$\min \arg_c Q(S(A_{circ}) - S(cA_{dens})),$$

wherein $A_{dens}$ is a densitometric area, $A_{circ}$ is a contour area found by segmentation, c is the conversion factor, S is a statistic on the areas, and Q is a difference function that quantifies the difference between the densitometric area $A_{dens}$ and the contour area $A_{circ}$.

38. A computer program medium according to claim 28, wherein:

the displacing of c) involves
i) displacement of at least one border inward relative to a given centerline position of the vessel portion, and
ii) recalculating the densitometric area for the given centerline position of the vessel portion according to the inward displacement of the at least one border in i).

39. A computer program medium according to claim 28, wherein:

the operations of i) and ii) are repeated for zero or more iterations until there is predetermined change in the densitometric area.

* * * * *